(12) United States Patent
Isch et al.

(10) Patent No.: US 11,324,497 B2
(45) Date of Patent: May 10, 2022

(54) STEP STAPLE FOR FRACTURE FIXATION

(71) Applicant: Biomet Manufacturing, LLC, Warsaw, IN (US)

(72) Inventors: Bryce A. Isch, Warsaw, IN (US); Kelly Lackey, Warsaw, IN (US); Brian K. Berelsman, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 138 days.

(21) Appl. No.: 16/483,239

(22) PCT Filed: Feb. 7, 2018

(86) PCT No.: PCT/US2018/017180
§ 371 (c)(1),
(2) Date: Aug. 2, 2019

(87) PCT Pub. No.: WO2018/148252
PCT Pub. Date: Aug. 16, 2018

(65) Prior Publication Data
US 2020/0008799 A1    Jan. 9, 2020

Related U.S. Application Data

(60) Provisional application No. 62/456,838, filed on Feb. 9, 2017.

(51) Int. Cl.
*A61B 17/064*    (2006.01)
*A61B 17/72*    (2006.01)
*A61B 17/68*    (2006.01)

(52) U.S. Cl.
CPC ...... *A61B 17/0642* (2013.01); *A61B 17/7291* (2013.01); *A61B 2017/681* (2013.01)

(58) Field of Classification Search
CPC .............. A61B 17/064; A61B 17/0642; A61B 17/0644; A61B 17/7291; A61B 17/68; A61B 2017/681
See application file for complete search history.

(56) References Cited

U.S. PATENT DOCUMENTS 5,282,861 A    2/1994    Kaplan
5,662,655 A    9/1997    Laboureau et al.
(Continued)

FOREIGN PATENT DOCUMENTS

CN    110312479 A    10/2019
EP    0354599 A1    2/1990
(Continued)

OTHER PUBLICATIONS

"European Application Serial No. 18751668.7, Extended European Search Report dated Dec. 4, 2020", 7 pgs.
(Continued)

*Primary Examiner* — Matthew J Lawson
*Assistant Examiner* — Lisa Nguyen
(74) *Attorney, Agent, or Firm* — Schwegman Lundberg & Woessner, P.A.

(57) ABSTRACT

Described herein are examples of illustrative orthopedic staples, systems and methods. In an illustrative orthopedic staple for fusion of a foot or ankle bone fracture, the staple includes a bridge, a first staple leg and a second staple legs. The bridge of the illustrative staple extends from a first end portion to a second end portion along a first direction. The bridge also includes a step down region located between the first end portion and the second end portion, the step down region having a height along the insertion axis of the staple. In some examples, the first staple leg has a first staple leg height extending from the bridge to the first distal tip and the second staple leg has a second staple leg height extending (Continued)

from the bridge to the second distal tip, and the first staple leg height is greater than the second staple leg height.

13 Claims, 4 Drawing Sheets

(56) References Cited

U.S. PATENT DOCUMENTS

| | | | |
|---|---|---|---|
| 11,058,426 B2* | 7/2021 | Nalagatla | A61L 31/022 |
| 2006/0235469 A1* | 10/2006 | Viola | A61B 17/0643 606/219 |
| 2008/0161808 A1 | 7/2008 | Fox | |
| 2016/0199060 A1* | 7/2016 | Morgan | A61B 17/068 227/175.1 |
| 2016/0270923 A1 | 9/2016 | Finley et al. | |

FOREIGN PATENT DOCUMENTS

| | | |
|---|---|---|
| FR | 2668921 A1 | 5/1992 |
| WO | WO-2016026029 A1 | 2/2016 |
| WO | WO-2018148252 A1 | 8/2018 |

OTHER PUBLICATIONS

"European Application Serial No. 18751668.7, Response filed Apr. 6, 2020 to Communication pursuant to Rules 161(2) and 162 EPC dated Sep. 25, 2019", 19 pgs.

"International Application Serial No. PCT/US2018/017180, International Search Report dated Apr. 6, 2018", 2 pgs.

"International Application Serial No. PCT/US2018/017180, Written Opinion dated Apr. 6, 2018", 8 pgs.

Levine, Brett R, et al., "Experimental and clinical performance of porous tantalum in orthopedic surgery", Biomaterials, (27), (Sep. 2006), 4671-81.

"European Application Serial No. 18751668.7, Response filed Jul. 1, 2021 to Extended European Search Report dated Dec. 4, 2020", 16 pgs.

* cited by examiner

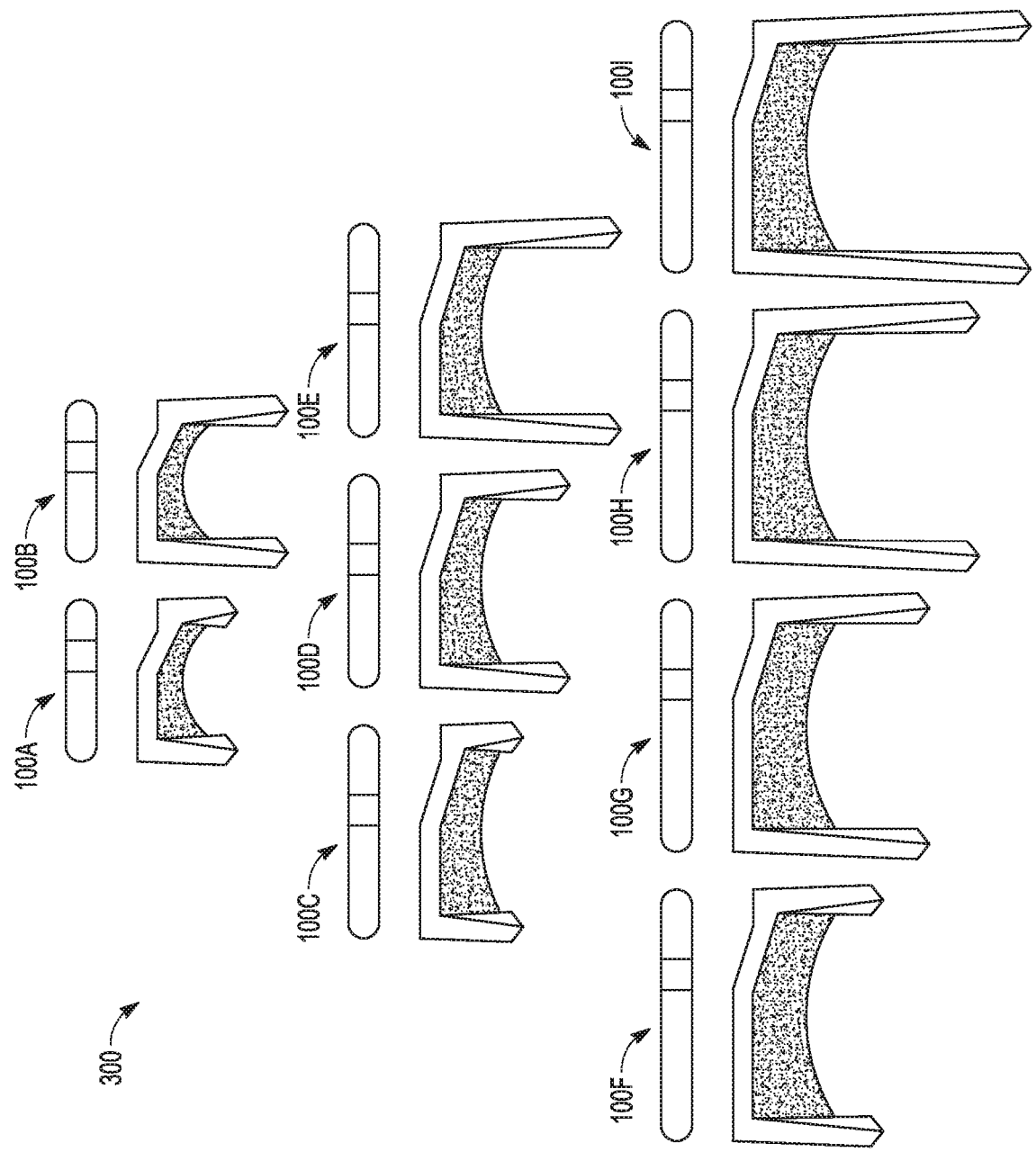

ure fixation

STEP STAPLE FOR FRACTURE FIXATION

CLAIM OF PRIORITY

This application is a U.S. National Stage Application under 35 U.S.C. 371 from International Application Serial No. PCT/US2018/017180 filed on Feb. 7, 2018, and published as WO 2018/148252 A1 on Aug. 16, 2018, which claims the benefit of priority to U.S. Provisional Application Ser. No. 62/456,838, filed on Feb. 9, 2017, each of which is incorporated herein by reference in its entirety.

TECHNICAL FIELD

This document pertains generally, but not by way of limitation, to orthopedic devices, and, more particularly, to orthopedic staples.

BACKGROUND

Bone fractures are a common occurrence that can be treated with surgical intervention. One type of intervention used to treat bone fractures is the use of bone staples to hold the bone fragments on either side of the fracture together. The implanted bone staple helps keep the bone fragments together so that they do not drift apart, allowing the bone to heal faster and reducing the risk of the fracture propagating through the bone.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 3 shows a system including a plurality of orthopedic staples 100 (e.g., 100a-100i). The staples are depicted including both top and side views combined; similar to the views FIGS. 1A and 1B.

DETAILED DESCRIPTION

Figure 1A:
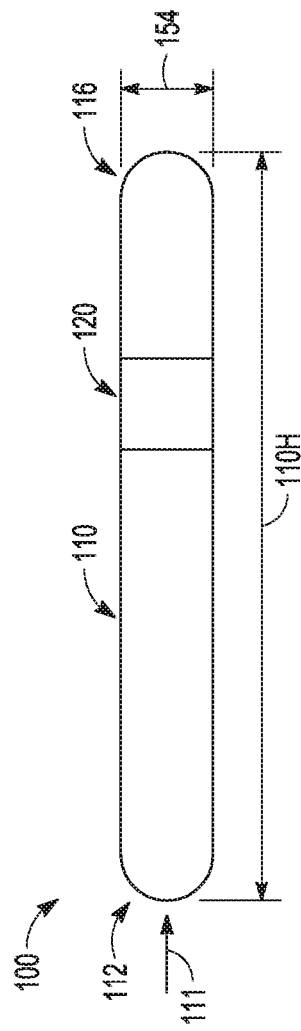
FIG. 1A is a top view of an illustrative example of an orthopedic staple.

As discussed above, bone fractures are a common occurrence that can be treated with surgical intervention. One type of intervention used to treat bone fractures is the use of orthopedic or bone staples that hold the bone fragments on either side of the fracture together. The implanted orthopedic staple helps to compress the bone fragments together so that they do not drift apart, allowing the bone to heal faster and reducing the risk of the fracture propagating through the bone.

Improved orthopedic staples, systems and methods are described herein. Including an orthopedic staple for fusion of a foot or ankle bone fracture.

One problem that can occur with orthopedic staples, is irritation of the soft tissues near the staple when the staple is implanted in the body. Conventional staples include a geometry that may result in a portion of the bridge (e.g., the top) of the staple protruding above the surface of the bone or one of the bone fragments. When a staple extends out of the bone surface, especially if it has a hard protrusion or prominence, it may impinge on the adjacent soft tissues and cause pain, discomfort, and potentially soft-tissue irritation.

To prevent a prominence from impinging on soft tissues, the orthopedic staples, systems and methods described herein include a staple having a curvature incorporated into the bridge of the staple (e.g., the top of the staple). The curvature may be selected from anatomic data corresponding to the bone morphology of the particular anatomic fusion site(s). A staple including a curved bridge that corresponds more closely to the size and shape of the implant site, reduces the likelihood of a prominence that results when a conventional staple extends out of the bone surface.

The staples, systems and methods described herein are well suited for fixation of the bones of the foot and ankle. Including, but not limited to, bones of the front foot, middle foot and hind foot. For example, the staple may be sized and shaped to be inserted at a Talonavicular (TN) fusion, a calcaneus cuboid (CC) fusion, a tibia talus (TT) fusion, a tarsal metatarsal (TMT) fusion, a navicular cuneiform (NC) fusion, 1st, 2nd, 3rd, a Lapidus (fusion of the metatarsal/cuneiform), a Lisfranc procedure or a calcaneus slide.

Other indications for use may include: hand and foot bone fragment and osteotomy fixation and joint arthrodesis, and fixation of proximal tibial metaphysis osteotomy. In addition, other appropriate uses include fixation of small bone fragments. These fragments may be located in long bones such as a femur, fibula and tibia in the lower extremities; the humerus, ulna or radius in the upper extremities; the clavicle and ribs; and flat bones such as the pelvis, scapula and sternum.

The bridge of the staple may be shaped corresponding to an anatomical structure of a bone surface surrounding these insertion sites and others. Although various uses have been disclosed herein, the staples, systems and methods may, however, be implanted in and used to fuse any suitable bones.

Figure 1B:
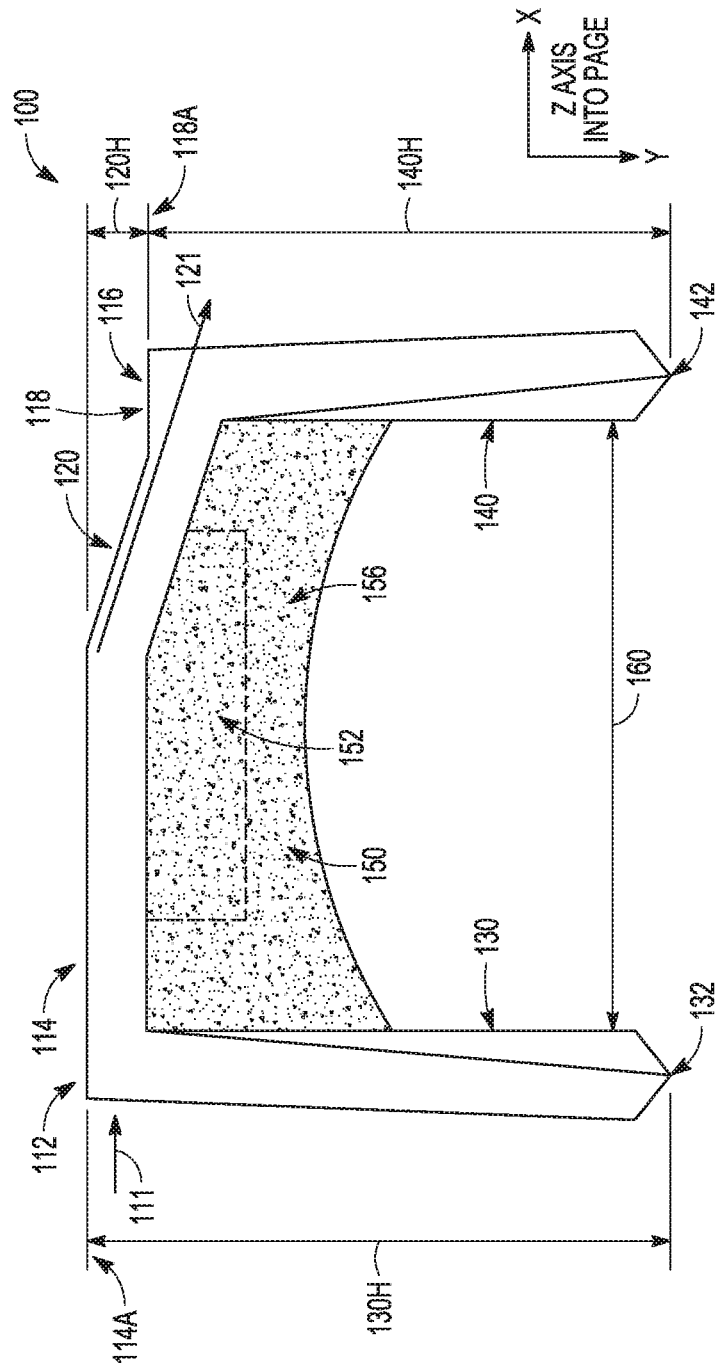
FIG. 1B is a side view of the staple of FIG. 1A.
Figure 2A:
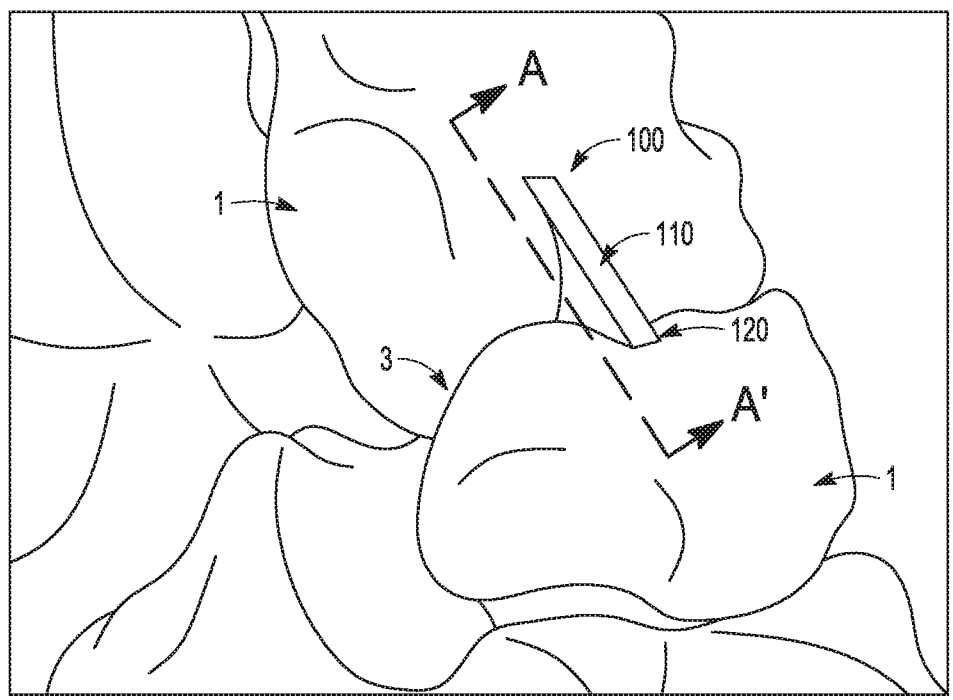
FIG. 2A is a perspective view of the staple of FIGS. 1A and 1B inserted into a bone.

FIGS. 1A and 1B show an illustrative example of an orthopedic staple 100 in top and side views in accordance with some examples. The illustrative staple 100 includes a bridge 110 and first and second staple legs 130, 140. The staple legs 130, 140 extend away from the bridge 110, such as along insertion axis Y (see, coordinates in FIG. 1B). The bridge 110 provides a structural connection between the staple legs 130, 140 such that when the staple legs 130, 140 are inserted into holes prepared in the bone 1, the staple 100 holds the bones at the fracture site 3 together so that fusing of bone along the fracture site 3 may occur (FIG. 2A).

As shown in FIGS. 1A and 1B, the bridge 110 extends from a first end portion 112 towards a second end portion 116 along a first direction 111. The bridge 110 also includes a step down region 120 between the first end portion 112 and the second end portion 116. The step down region 120 may be described as extending in a both the first direction and a second direction 121 that is different from the first direction 111. The step down region 120 includes a transition portion having a contour. The contour may correspond to, or according to, a contour of the bone to be fused (e.g., the surface of the bone).

Another way of describing the bridge 110 shown in FIGS. 1A and 1B is that the bridge 110 extends from the first end portion 112 to a second end portion 116. The first end portion 112 having a first surface 114 lying in a first plane 114a. The second end portion 116 having a second surface 118 lying in a second plane 118a. The bridge 110 further including a step down region 120 between the first end portion 112 and the second end portion 116. The step down region 120 being contoured to include a transition surface between the first surface 114 and the second surface 118. The contour may approximate a surface of a bone 1.

In some examples, the bone that the step down region 120 is contoured to approximate is a surface of a bone of a foot. The step down region 120 may also be contoured to approximate the surface of a bone of an ankle. The step down region 120 may be contoured according to the contour of any suitable bone that may be fixated by the staple 100.

As shown in FIGS. 1A and 1B, the step down region 120 may be biased along the bridge 110, with the step down region 120 located closer to the second staple leg 140 than the first staple leg 130.

In some examples, the contour of the staple 100 corresponds to the contour of the bone fracture to be fused. This contour may be determined based on, or according to, data stored in an anatomic database. For example, ZiBRA™ Analytical Modeling System is one such an anatomic database from Zimmer, Inc., of Warsaw, Ind. ZiBRA™ is a database used to collect and analyze anatomic data. The operating thesis for ZiBRA™ is that when used to design orthopedic components they will conform better to the anatomy and provide increased clinical options. The ZiBRA™ software application enables: statistical shape analysis, virtual surgery, component placement optimization, and implant fit assessment.

The step down region 120 has a step down region height 120h that may be described as extending along the insertion axis of the staple 100. The height of the step down region may be described with reference to FIG. 1A as the distance along the insertion axis between the first surface 114a and the second surface 118a. The height of the step down region 120 may be less than 4.0 mm. In some examples, it may be preferable for the step down region 120 to be in a range between about 0.5 mm and 4.0 mm. In some examples, it may be preferable for the step down region 120 to be in a range of about 0.5 to 2.5 mm.

Alternatively, the step down region 120 could include a more complex curvature than depicted in the illustrative staple 100. For example, in some examples, the height of the step down region 120h may be described as the maximum step down from the first surface 114a of the bridge 110 to the lowest surface of the bridge with respect to the insertion axis Y (in the illustrative example this lowest surface is element 118a). In some examples, this lowest point may not occur at the second end portion 116, but rather, at a point between the first end portion 112 and the second end portion 116. In other words, the bridge 110 could include a portion having a surface shape that may be very generally described as having a concave portion included in the step down region. Further, alternative examples could also include a surface shape that may be described very generally as having a convex portion included in the step down portion. These and other step down regions are considered to be within the scope of this disclosure.

The height of the step down region 120h will be described further in relation to the height of the staple legs 130, 140 below.

The staple 100 legs may include first and second staple legs 130, 140 extending from the bridge 110. For example, as shown in FIGS. 1A and 1B, the first staple leg 130 extends from the first end portion 112 of the bridge 110 to a first distal tip 132 of the first staple leg 130. The second staple leg 140 extends from the second end portion 116 of the bridge 110 to a second distal tip 142 of the second staple leg 140.

Also as depicted in FIGS. 1A and 1B, the first staple leg 130 may have a first staple leg height 130h that extends from the bridge 110 to the first distal tip 132. Likewise, the second staple leg 140 may have a second staple leg height 140h that extends from the bridge 110 to the second distal tip 142. In the illustrative example, the first staple leg height 130h is greater than the second staple leg height 140h.

Figure 2B:
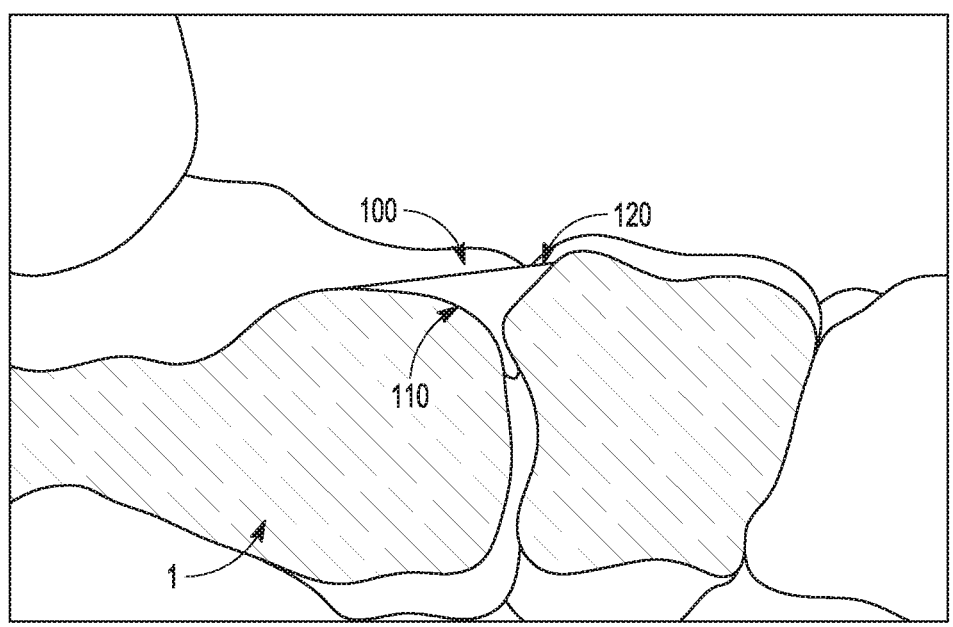
FIG. 2B is a cross-sectional side view of the staple of FIGS. 1A and 1B inserted into a bone along line A-A' in FIG. 2A.

As previously described, the step down region 120 may be biased along the bridge 110 to be located closer to the second staple leg 140 than the first staple leg 130. Depending on the contour of the surface of the bone 1 (FIGS. 2A and 2B), this bias may be located closer to the second staple leg 140 than to the first staple leg 130. In certain cases, this may be considered a more preferred example. In other examples, the step down region 120 may be biased along the bridge 110 to be located closer to the first staple leg 130 than the second staple leg 140.

As previously discussed, the step down region 120 may include a step down region height 120h. In some examples, and as shown in FIGS. 1A and 1B, the height of the step down region 120 may be approximately equal to difference in height between the first staple leg 130 and the second staple leg 140. As used herein, the term approximately may be used to define normal design and manufacturing tolerances, or within, for example, ±10%.

In some examples, the first end portion 112 could include the portion of the bridge 110 that the first staple leg 130 extends from, but could also include a portion of the bridge 110 that extends outward (away from a centerline) past the location where the bridge 110 and the staple 100 leg join together. Likewise, the second end portion 116 may include the portion of the bridge 110 that the second staple leg 140 extends from, and also includes a portion of the bridge 110 that extends outward in the other direction past the location where the bridge 110 and staple 100 leg join together. In such an example, the bridge length 110h may be wider than depicted in the FIGS., and is not limited to the illustrative examples in the FIGS. These and other designs are considered to be within the scope of this disclosure.

Any portion of the staple, or the entire staple, including the bridge and/or the staple legs may be formed of any suitable material, including, but not limited to, titanium, including porous or solid titanium.

In some examples, the staple 100 may include a central portion 150 disposed along the bridge 110 between the first end portion 112 and the second end portion 116. For example, the central portion 150 may be disposed between the first staple leg 130 and the second staple leg 140. The central portion 150 may include a structure that supports boney ingrowth, such as, but not limited to, a porous structure, such as porous titanium.

In FIGS. 1A and 1B, the central portion 150 is shown as spanning the entire distance between the first staple leg 130 and the second staple leg 140. In some examples the central portion 150 may span only a portion of the distance from the first staple leg 130 to the second staple leg 140, or intermittently span the distance. Any suitable geometry that supports boney ingrowth in the central portion 150 may be provided.

The central portion 150 may be made entirely of a porous structure 156, or the central portion 150 may be formed as a core 152 having a porous structure 156 around the core 152. In some examples the core 152 may be a solid core 152. In some examples, the core 152 and the porous structure may be integrally formed by the same machine, however this is not required. In some examples the staple 100, including the central portion 150 may be formed on a 3D printer. In some examples, the entire staple 100, or only portions of the staple 100 may be integrally formed by 3D printing. Any other suitable manufacturing method(s) may be used to form the staple 100, and any number of steps or machines may be employed.

As shown in FIG. 1A, the central portion 150 may be formed with a constant or varying thickness 154. The thickness 154 may also be visualized as the thickness of the central portion in a direction Z into the page in FIG. 1B.

The thickness 154 of the central portion 150 may be constant or variable. For example, in some examples, the thickness 154 of the central portion 150 may vary between about 0.5 mm and 4.0 mm. In some examples, the thickness 154 of the central portion 150 may preferably vary between about 0.9 mm and 2.0 mm thick at different points along the insertion axis Y. The thickness 154 may vary along the insertion axis Y, or in any other direction. Any suitable thickness 154, or range of thicknesses 154 may be provided depending on the size and type of staple 100, and the application to which the staple 100 is being applied.

To facilitate boney ingrowth, the central portion 150 may be formed of a three-dimensional structure that supports bony ingrowth. For example, a highly porous, three-dimensional metallic structure may be provided that incorporates one or more of a variety of biocompatible metals such as but not limited to titanium, a titanium alloy, cobalt chromium, cobalt chromium molybdenum, tantalum, a tantalum alloy, niobium, or alloys of tantalum and niobium with one another or with other metals. Such structures are particularly suited for contacting bone and/or soft tissue, and in this regard, can be useful as bone substitutes and other implants and implant components that are receptive to cell and tissue ingrowth, for example, by allowing bony tissue or other tissue to grow into the porous structure over time to enhance fixation (e.g., osseointegration) between the structure and surrounding bodily structures. According to certain examples of the present disclosure, an open porous metal structure, or a portion thereof, may have a bulk porosity as low as 55%, 65%, or 75% or as high as 80%, 85%, or 90%, or within any range defined between any pair of the foregoing values, and in this regard, such structures can provide lightweight, yet strong porous implants. Certain porous metal structures, despite having such high porosities, are capable of withstanding extreme mechanical loads at the time of implantation and over long periods of time, for example, where a highly porous, three-dimensional metallic structure is forcefully impacted and press fit into a bone, by itself or connected to another implant, and maintains its shape during impaction and following many months or years of service in the body. Such structures can be manufactured according to any suitable technique or process. An example of an open porous metal structure is produced using Trabecular Metal™ Technology available from Zimmer, Inc., of Warsaw, Ind. Trabecular Metal™ is a trademark of Zimmer, Inc. Such a material may be formed from a reticulated vitreous carbon foam substrate which is infiltrated and coated with a biocompatible metal, such as tantalum, by a chemical vapor deposition ("CVD") process in the manner disclosed in detail in U.S. Pat. No. 5,282,861 and in Levine, B. R., et al., "Experimental and Clinical Performance of Porous Tantalum in Orthopedic Surgery", Biomaterials 27 (2006) 4671-4681, the disclosures of which are expressly incorporated herein by reference.

In some instances, a highly porous, three-dimensional metallic structure will be fabricated using a selective laser sintering (SLS) or other additive manufacturing-type process such as direct metal laser sintering or electron beam melting. In one example, a three-dimensional porous article is produced in layer-wise fashion from a laser-fusible powder, e.g., a single-component metal powder, which is deposited one layer at a time. The powder is fused, remelted or sintered, by the application of laser energy that is directed to portions of the powder layer corresponding to a cross section of the article. After the fusing of the powder in each layer, an additional layer of powder is deposited, and a further fusing step is carried out, with fused portions or lateral layers fusing so as to fuse portions of previous laid layers until a three-dimensional article is complete. In certain examples, a laser selectively fuses powdered material by scanning cross-sections generated from a 3-D digital description of the article, e.g., from a CAD file or scan data, on the surface of a powder bed. Complex geometries can be created using such techniques, and in some instances, net shape and near net shape implants are constructed. In some examples, a non-porous or essentially non-porous base substrate will provide a foundation upon which a three-dimensional porous structure will be built and fused thereto using a selective laser sintering (SLS) or other additive manufacturing-type process. Such substrates can incorporate one or more of a variety of biocompatible metals such as any of those disclosed herein.

Generally, a highly porous, three-dimensional metallic structure will include a large plurality of ligaments that define open voids (e.g., pores) or channels between the ligaments. The open spaces between the ligaments form a matrix of continuous channels having few or no dead ends, such that growth of soft tissue and/or bone through the open porous metal is substantially uninhibited. According to some aspects of the present disclosure, exterior surfaces of an open porous metal structure can feature terminating ends of the above-described ligaments. Such terminating ends can be referred to as struts, and they can generate a high coefficient of friction along an exposed porous metal surface. Such features can impart an enhanced affixation ability to an exposed porous metal surface for adhering to bone and soft tissue. Also, when such highly porous metal structures are coupled to an underlying substrate, a small percentage of the substrate may be in direct contact with the ligaments of the highly porous structure, for example, approximately 15%, 20%, or 25%, of the surface area of the substrate may be in direct contact with the ligaments of the highly porous structure.

A highly porous, three-dimensional metallic structure may be fabricated such that it comprises a variety of densities in order to selectively tailor the structure for particular orthopedic applications, for example, by matching the structure to surrounding natural tissue in order to provide an improved matrix for tissue ingrowth and mineralization. Such structures can be isotropic or anisotropic. In this regard, according to certain examples, an open porous metal structure may be fabricated to have a substantially uniform porosity, density, void (pore) size, pore shape, and/or pore orientation throughout, or to have one or more features such as porosity, density, void (pore) size, pore shape, and/or pore orientation being varied within the structure, or within a portion thereof. For example, an open porous metal structure may have a different pore size, pore shape, and/or porosity at different regions, layers, and surfaces of the structure. The ability to selectively tailor the structural properties of the open porous metal enables, for example, tailoring of the structure for distributing stress loads throughout the surrounding tissue and promoting specific tissue ingrown within the open porous metal. In some instances, a highly porous, three-dimensional metallic structure, once formed, will be infiltrated and coated with one or more coating materials such as biocompatible metals such as any of those disclosed herein.

In some examples, the porous metal structure can be a formed from a titanium alloy using an additive manufacturing process, such as with OsseoTi™, which is commercially available from Biomet Manufacturing, LLC (Warsaw, Ind., USA). Briefly, however, OsseoTi is highly biocompatible, has high corrosion resistance and includes a highly interconnected porous architecture that mimics the porous structure of human cancellous bone, which can enhance bone integration and in-growth. In one exemplary implementation, OsseoTi can include a porous construct with a porosity.

FIG. 3 shows an illustrative example of a system 300 including a plurality of orthopedic staples 100A-100I. The staples 100A-100I are depicted including both top and side views together in a manner similar to the combination of FIGS. 1A and 1B. The numerous examples of staple geometries are merely provided as non-limiting examples of possible staple 100 geometries in accordance with this disclosure.

The plurality of staples 100A-100I may be provided in a variety of sizes and shapes that correspond to a variety of potential anatomic fusion sites that the staple 100 may be used to treat. The staples 100A-100I could also be provided in a variety of different sizes to accommodate variations in fracture site geometry or severity, or a variety of different patient skeletal sizes.

For example, in the illustrative system 300, if the surgeon was performing a Talonavicular (TN) fusion, the surgeon would select a staple 100 that is be sized and/or shaped to be implanted within this specific anatomic region 120. Other common anatomic regions and fusion sites within the foot anatomy for which staples 100 may be provided as part of the system 300 may include: a calcaneus cuboid (CC) fusion, a tibia talus (TT) fusion, a tarsal metatarsal (TMT) fusion, a navicular cuneiform (NC) fusion, 1st, 2nd, 3rd, Lapidus (fusion of the metatarsal/cuneiform), a Lisfranc procedure or a calcaneus slide. In addition, other appropriate uses include fixation of any small bone fragments. These fragments may be located in long bones such as a femur, fibula and tibia in the lower extremities; the humerus, ulna or radius in the upper extremities; the clavicle and ribs; and flat bones such as the pelvis, scapula and sternum.

The bridge of the staple may be shaped corresponding to an anatomical structure of a bone surface surrounding these insertion sites and others. Although various uses have been disclosed herein, the staples, systems and methods may, however, be implanted in and used to fuse any suitable bones.

In the illustrative example of the system 300, the system 300 includes the plurality of orthopedic staples 100, such as a first staple (e.g., 100A) and a second staple (e.g., 100B). Similarly to the staple of FIGS. 1A and 1B, the first staple 100a having a bridge 110 of a first extent (e.g., FIG. 1A, 100H) between a first end portion 112 and a second end portion 116. As previously described with respect to the illustrative staple 100 above. The bridge 110 includes a step down region 120 between the first end portion 112 and the second end portion 116, the step down region 120 having a first height (e.g., FIG. 1A, 120H). To facilitate insertion of the staple 100 into holes prepared in the bone 1, the first staple 100 includes first and second staple legs 130, 140 extending away from the bridge 110.

Similarly to the first staple 100a, and the staple 100 of FIGS. 1A and 1B, the second staple (e.g., 100B) of the system 300 may have a bridge 110 of a second extent (e.g., FIG. 1A, 100H) between a first end portion 112 and a second end portion 116, the bridge 110 including a step down region 120 between the first end portion 112 and the second end portion 116, the step down region 120 having a second height (e.g., FIG. 1A, 120H). Like the first staple 100A, the second staple 100B also includes respective first and second staple legs 130, 140 extending away from the bridge 110 of the second staple 100.

The plurality of staples 100A-100I may be of different size and shape. For example, the second staple 100B may include a second extent (e.g., FIG. 1A, 120H) that is different from the first extent (e.g., FIG. 1A, 120h) of the first staple 100. In addition, or alternatively, the second step down region 120 of the second staple 100 may be different from the first step down region 120 of the first staple 100. As previously described, the differences in the step down regions 120 may include different heights or curvatures, as well as other geometric or structural differences.

Figure 4:
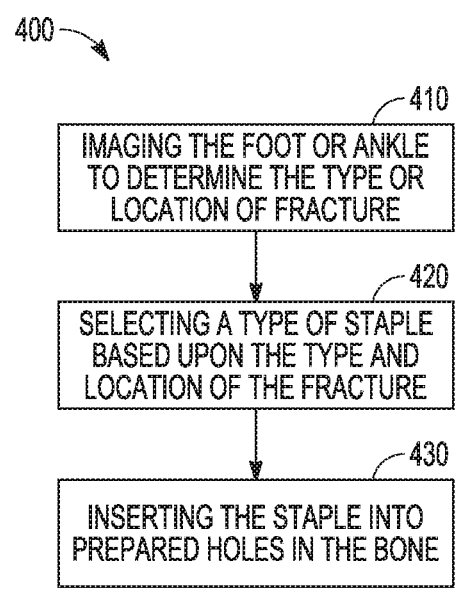
FIG. 4 is a flow chart illustrating an example of a method of fusing bone tissue at a fracture site in a foot or ankle bone of a patient.

FIG. 4 is a flow chart illustrating an example of a method 400 of fusing bone tissue at a fracture site 3 in a foot or ankle bone of a patient. The illustrative method 400 may be applied to the staple 100 and/or system 300 described above. The illustrative method 400 may also be applied to other staples and systems.

As shown in FIG. 4, the illustrative method 400 of fusing bone at a fracture site 3 in a foot or ankle bone of a patient may include the following steps. The illustrative method 400 may begin with step 410 including imaging the foot or ankle of the patient to determine a type or location of the fracture (e.g., FIG. 2A, fracture site 3). Determining the type or location could also involve determining the bone(s) involved in the fracture.

Upon determining the type or location of the fracture, step 420 includes selecting a type of staple 100 based upon the type or location of the fracture 3. In the selecting step 420, the staple 100 selected may be chosen because it is shaped, sized and configured based upon the type or location of the fracture 3 to have a bridge 110 that corresponds to the anatomy of the bone 1. The staple 100, and in particular the bridge 110 shape be may correspond to (e.g., reflect, be determined based on, formed according to) known bone surfaces and in reference to bone dimensions and characteristics provided in an anatomic database. Further, the bridge 110 may have a predetermined length, including a step down region 120 of the bridge 110 to be of a predetermined height. The staple 100 legs may also be located a predetermined distance apart, and the height of one staple (e.g., 130) leg may be longer than the height of the other staple leg (e.g., 140).

Using the selected staple 100, step 430 of the illustrative method 400 includes inserting the staple 100 legs into holes that have been prepared in the bone. Step 430 may include inserting the staple 100 legs at least partially into the bone, or inserting the staple 100 until at least a portion of the bridge 110 is flush with the surface of the bone.

The illustrative method 400 is merely one example of a method 400 that may be used with the staple 100 and system 300 described herein. Method 400 is not limited to steps 410, 420 and 430. The method 400 may include fewer steps or additional method 400 steps other than those specified herein.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

Numbered Examples

Example 1 is an orthopedic staple for fusion of a foot or ankle bone fracture, the staple comprising: a bridge extending from a first end portion to a second end portion along a first direction, the bridge including a step down region between the first end portion and the second end portion, wherein the step down region extends in both the first direction and a second direction that is different from the first direction, the step down region including a transition portion having a contour corresponding to a contour of the bone fracture to be fused; a first staple leg extending from the first end portion to a first distal tip; and a second staple leg extending from the second end portion to a second distal tip.

In Example 2, the subject matter of Example 1 optionally includes a central portion disposed along the bridge between the first staple leg and the second staple leg, the central portion having a structure that supports boney ingrowth.

In Example 3, the subject matter of any one or more of Examples 1-2 optionally include a central portion disposed along the bridge between the first staple leg and the second staple leg, the central portion comprising a solid core and a porous structure around the solid core that supports boney ingrowth.

In Example 4, the subject matter of any one or more of Examples 1-3 optionally include wherein the step down region is contoured according to the contour of the bone fracture to be fused.

In Example 5, the subject matter of any one or more of Examples 1-4 optionally include wherein the bone that the step down region is contoured to approximate is a surface of a bone of a foot.

In Example 6, the subject matter of any one or more of Examples 1-5 optionally include wherein the first staple leg has a first staple leg height extending from the bridge to the first distal tip, and wherein the second staple leg has a second staple leg height extending from the bridge to the second distal tip, and wherein first staple leg height is greater than the second staple leg height.

In Example 7, the subject matter of Example 6 optionally includes wherein the step down region has a height along the insertion axis of the staple, and wherein the difference between the first staple leg height and the second staple leg height is approximately equal to the height of the step down region.

In Example 8, the subject matter of any one or more of Examples 6-7 optionally include wherein the step down region is biased along the bridge to be closer to the second staple leg than the first staple leg.

In Example 9, the subject matter of any one or more of Examples 1-8 optionally include wherein the contour of the staple corresponds to the contour of the bone fracture to be fused according to anatomic data stored in an anatomic database.

In Example 10, the subject matter of any one or more of Examples 1-9 optionally include a thickness of the central portion in a range between 0.5 mm and 4.0 mm.

In Example 11, the subject matter of any one or more of Examples 7-10 optionally include the height of the step down region is in a range between 0.5 mm and 4.0 mm.

In Example 12, the subject matter of any one or more of Examples 1-11 optionally include a staple sized to be inserted at: a talonavicular fusion, a calcaneus cuboid (CC) fusion, a tibia talus (TT) fusion, a tarsal metatarsal (TMT) fusion, a navicular cuneiform (NC) fusion, 1st, 2nd, 3rd, Lapidus (fusion of the metatarsal/cuneiform), a Lisfranc procedure or a calcaneus slide, the staple having a bridge shaped corresponding to an anatomical structure of a bone surface surrounding the insertion site.

Example 13 is an orthopedic staple comprising: a bridge extending from a first end portion to a second end portion, the first end portion having a first surface lying in a first plane, and the second end portion having a second surface lying in a second plane, the bridge further including a step down region between the first end portion and the second end portion, wherein the step down region includes a transition surface between the first surface and the second surface; a first staple leg extending away from the first end portion; and a second staple leg extending away from the second end portion.

In Example 14, the subject matter of Example 13 optionally includes a central portion disposed along the bridge between the first staple leg and the second staple leg, the central portion having a structure that supports boney ingrowth.

In Example 15, the subject matter of any one or more of Examples 13-14 optionally include a central portion disposed along the bridge between the first staple leg and the second staple leg, the central portion comprising a core and a structure around the core that supports boney ingrowth.

In Example 16, the subject matter of any one or more of Examples 13-15 optionally include wherein the central portion comprises a porous structure.

In Example 17, the subject matter of any one or more of Examples 13-16 optionally include wherein the central portion comprises a solid core within a porous structure.

In Example 18, the subject matter of any one or more of Examples 13-17 optionally include wherein the staple legs are formed of solid titanium.

In Example 19, the subject matter of any one or more of Examples 13-18 optionally include wherein the step down region is contoured according to the contour of a bone fracture to be fused.

In Example 20, the subject matter of any one or more of Examples 13-19 optionally include wherein the step down region is contoured according to a bone of the foot.

In Example 21, the subject matter of any one or more of Examples 13-20 optionally include wherein the transition surface of the staple corresponds to the contour of the bone fracture to be fused according to anatomic data stored in an anatomic database.

Example 22 is a method of fusing bone at a fracture site in a foot or ankle bone of a patient, the fracture site including holes prepared in the bone, the method comprising the steps of: imaging the foot or ankle of the patient to determine a type or location of the fracture; selecting a type of staple based upon the type or location of the fracture, the staple being shaped, sized and configured in reference to an anatomic database, and based upon the type or location of the fracture, the bridge having a predetermined length, including a step down region of the bridge to be of a predetermined height, and staple legs being located a predetermined distance apart, wherein the height of one staple leg is longer than the height of the other staple leg; and inserting the staple legs into the prepared holes in the bone.

In Example 23, the subject matter of Example 22 optionally includes wherein the staple further comprises a central portion disposed along the bridge between the staple legs, the central portion having a structure that supports boney ingrowth.

In Example 24, the subject matter of any one or more of Examples 22-23 optionally include wherein inserting the staple legs at least partially into the bone includes inserting the staple until at least a portion of the bridge is flush with the surface of the bone.

Example 25 is a system including a plurality of orthopedic staples, the system comprising: a first staple having: a bridge of a first extent between a first end portion and a second end portion, the bridge including a step down region between the first end portion and the second end portion, the step down region having a first height; first and second staple legs extending away from the bridge; and a second staple having: a bridge of a second extent between a first end portion and a second end portion, the bridge including a step down region between the first end portion and the second end portion, the step down region having a second height; first and second staple legs extending away from the bridge; wherein the second extent is different from the first extent, and wherein the second step down region is different from the first step down region.

In Example 26, the subject matter of Example 25 optionally includes wherein each of the first and second staples comprise: a first staple leg having a height extending away from the first end portion to a first distal tip; a second staple leg having a height extending away from the second end portion to a second distal tip, wherein the height of the first staple leg of the first staple is longer than the height of the second staple leg of the first staple, and wherein the height of the first staple leg of the second staple is longer than the height of the second staple leg of the second staple.

In Example 27, the subject matter of any one or more of Examples 25-26 optionally include wherein the first staple has a central portion disposed along the bridge between the first staple leg and the second staple leg, and the second staple has a central portion disposed along the bridge between the first staple leg and the second staple leg, where the central portion has a structure that supports boney ingrowth.

In Example 28, an orthopedic staple for fusion of a foot or ankle bone fracture, the staple can optionally include: a bridge extending from a first end portion to a second end portion along a first direction, the bridge including a step down region between the first end portion and the second end portion, wherein the step down region extends in both the first direction and a second direction that is different from the first direction, the step down region including a transition portion having a contour corresponding to a contour of the bone fracture to be fused; a first staple leg extending from the first end portion to a first distal tip in the second direction, wherein the first staple leg has a first staple leg height extending from the bridge to the first distal tip; a second staple leg extending from the second end portion to a second distal tip in the second direction, wherein the second staple leg has a second staple leg height extending from the bridge to the second distal tip, and wherein first staple leg height is greater than the second staple leg height; and a central portion disposed along the bridge between the first staple leg and the second staple leg, the central portion having a structure that supports boney ingrowth.

In Example 29, the staple of Example 28, can optionally include the central portion comprising a solid core and a porous structure around the solid core that supports the boney ingrowth.

In Example 30, the staple of any one or any combination of Examples 28-29 can optionally include the bone that the transition portion of the step down region is contoured to approximate is a surface of a bone of a foot.

In Example 31, the staple of any one or any combination of Examples 28-30 can optionally include the step down region has a height along the insertion axis of the staple, and wherein the difference between the first staple leg height and the second staple leg height is approximately equal to the height of the step down region.

In Example 32, the staple of any one or any combination of Examples 28-31 can optionally include the step down region is biased along the bridge to be closer to the second staple leg than the first staple leg.

In Example 33, the staple of any one or any combination of Examples 28-32 can optionally include the contour of the staple corresponds to the contour of the bone fracture to be fused according to anatomic data stored in an anatomic database.

In Example 34, the staple of any one or any combination of Examples 28-33 can optionally include a thickness of the central portion is in a range between 0.5 mm and 4.0 mm.

In Example 35, the staple of any one or any combination of Examples 28-34 can optionally include a height of the step down region is in a range is less than 4.0 mm.

In Example 36, the staple of any one or any combination of Examples 28-35 can optionally include the staple is sized to be inserted at least one of a talonavicular (TN) fusion, a calcaneus cuboid (CC) fusion, a tibia talus (TT) fusion, a tarsal metatarsal (TMT) fusion, a navicular cuneiform (NC) fusion, 1st, 2nd, 3rd, Lapidus (fusion of the metatarsal/cuneiform), a Lisfranc procedure or a calcaneus slide, the bridge is shaped corresponding to an anatomical structure of a bone surface surrounding the insertion site.

In Example 37, an orthopedic staple can optionally include: a bridge extending from a first end portion to a second end portion, the first end portion having a first surface lying in a first plane, and the second end portion having a second surface lying in a second plane, the bridge further including a step down region between the first end portion and the second end portion that causes a disparity between a location of the first plane and a location of the second plane, wherein the step down region includes a transition surface between the first surface and the second surface having a contour; a first staple leg extending away from the first end portion to a first distal tip, wherein the first staple leg has a first staple leg height extending from the bridge to the first distal tip; a second staple leg extending away from the second end portion to a second distal tip, wherein the second staple leg has a second staple leg height extending from the bridge to the second distal tip, and wherein first staple leg height is greater than the second staple leg height; and wherein the staple is sized to be inserted at least one of a talonavicular (TN) fusion, a calcaneus cuboid (CC) fusion, a tibia talus (TT) fusion, a tarsal metatarsal (TMT) fusion, a navicular cuneiform (NC) fusion, 1st, 2nd, 3rd, Lapidus (fusion of the metatarsal/cuneiform), a Lisfranc procedure or a calcaneus slide, and wherein the bridge is shaped corresponding to an anatomical structure of a bone surface surrounding the insertion site and the contour is shaped corresponding to a contour of the bone fracture to be fused.

In Example 38, the staple of Example 37, can further include a central portion disposed along the bridge between the first staple leg and the second staple leg, the central portion having a structure that supports boney ingrowth.

In Example 39, the staple of Example 37 can further include a central portion disposed along the bridge between the first staple leg and the second staple leg, the central portion comprising a core and a structure around the core that supports boney ingrowth.

In Example 40, the staple of any one or any combination of Examples 38-39 can optionally include the central portion comprises a porous structure.

In Example 41, the staple of any one or any combination of Examples 37-40 the first staple leg and the second staple leg are formed of solid titanium.

In Example 42, the staple of any one or any combination of Examples 37-41 the transition surface of the staple corresponds to the contour of the bone fracture to be fused according to anatomic data stored in an anatomic database.

In Example 43, a method of fusing bone at a fracture site in a foot or ankle bone of a patient, the fracture site including holes prepared in the bone, the method can optionally include the steps of: imaging the foot or ankle of the patient to determine a type or location of the fracture; selecting a type of staple based upon the type or location of the fracture, the staple being shaped, sized and configured in reference to an anatomic database, and based upon the type or location of the fracture, the bridge having a predetermined length, including a step down region of the bridge to be of a predetermined height, and staple legs being located a predetermined distance apart, wherein the height of one staple leg is longer than the height of the other staple leg; and inserting the staple legs into the prepared holes in the bone.

In Example 44, the method of Example 43, wherein the staple can optionally further comprise a central portion disposed along the bridge between the staple legs, the central portion having a structure that supports boney ingrowth.

In Example 45, the method of any one or any combination of Examples 43-44, wherein inserting the staple legs at least partially into the bone includes inserting the staple until at least a portion of the bridge is flush with a surface of the bone.

In Example 46, a system including a plurality of orthopedic staples, the system can optionally include: a first staple having: a bridge of a first extent between a first end portion and a second end portion, the bridge including a step down region between the first end portion and the second end portion, the step down region having a first height as measured in a first direction; a first staple leg extending from the first end portion to a first distal tip in the first direction, wherein the first staple leg has a first staple leg height extending from the bridge to the first distal tip; a second staple leg extending from the second end portion to a second distal tip in the first direction, wherein the second staple leg has a second staple leg height extending from the bridge to the second distal tip, and wherein first staple leg height is greater than the second staple leg height due to the step down region having the first height; and a second staple having: a bridge of a second extent between a first end portion and a second end portion, the bridge including a step down region between the first end portion and the second end portion, the step down region having a second height; a first staple leg extending from the first end portion to a first distal tip in the first direction, wherein the first staple leg has a first staple leg height extending from the bridge to the first distal tip; and a second staple leg extending from the second end portion to a second distal tip in the first direction, wherein the second staple leg has a second staple leg height extending from the bridge to the second distal tip, and wherein first staple leg height is greater than the second staple leg height; wherein the second extent is different from the first extent, and wherein the second step down region is different from the first step down region such that the first height is different from the second height.

In Example 47, the system of Example 46 can optionally include: the height of the first staple leg of the first staple is longer than the height of the second staple leg of the first staple, and the height of the first staple leg of the second staple is longer than the height of the second staple leg of the second staple.

In Example 48, the system of any one or any combination of Examples 46-47 can optionally include the first staple has a central portion disposed along the bridge between the first staple leg and the second staple leg, and the second staple has a central portion disposed along the bridge between the first staple leg and the second staple leg, where the central portion has a structure that supports boney ingrowth.

In Example 49, any one or any combination of the systems, methods and/or apparatuses as previously provided in Examples 1-48 can optionally be configured such one or more (including all) the elements, features or options recited are available to use or select from.

What is claimed is:

1. An orthopedic staple for fusion of a foot or ankle bone fracture, the staple comprising:
   a bridge extending from a first end portion to a second end portion along a first direction, the bridge including a step down region between the first end portion and the second end portion, wherein the step down region extends in both the first direction and a second direction that is different from the first direction, the step down region including a transition portion having a contour corresponding to a contour of the bone fracture to be fused;
   a first staple leg extending from the first end portion to a first distal tip in the second direction, wherein the first staple leg has a first staple leg height extending from the bridge to the first distal tip;
   a second staple leg extending from the second end portion to a second distal tip in the second direction, wherein the second staple leg has a second staple leg height extending from the bridge to the second distal tip, and wherein the first staple leg height is greater than the second staple leg height; and
   a central portion disposed along the bridge between the first staple leg and the second staple leg, the central portion having a structure that supports boney ingrowth,
   wherein the contour of the staple corresponds to the contour of the bone fracture to be fused according to anatomic data stored in an anatomic database.

2. The staple of claim 1, wherein the central portion comprising a solid core and a porous structure around the solid core that supports the boney ingrowth.

3. The staple of claim 1, wherein the bone that the transition portion of the step down region is contoured to approximate is a surface of a bone of a foot.

4. The staple of claim 1, wherein the step down region has a height along an insertion axis of the staple, and wherein the difference between the first staple leg height and the second staple leg height is approximately equal to the height of the step down region.

5. The staple of claim 1, wherein the step down region is biased along the bridge to be closer to the second staple leg than the first staple leg.

6. The staple of claim 1, wherein the staple is sized to be inserted at least one of a talonavicular (TN) fusion, a calcaneus/cuboid (CC) fusion, a tibia/talus (TT) fusion, a tarsal/metatarsal (TMT) fusion, a navicular cuneiform (NC) fusion, 1st, 2nd, 3rd, Lapidus (fusion of the metatarsal/cuneiform), a Lisfranc procedure or a calcaneus slide, the bridge is shaped corresponding to an anatomical structure of a bone surface surrounding an insertion site.

7. An orthopedic staple for fusion of a foot or ankle bone fracture, the staple comprising:
   a bridge extending from a first end portion to a second end portion along a first direction, the bridge including a step down region between the first end portion and the second end portion, wherein the step down region extends in both the first direction and a second direction that is different from the first direction, the step down region including a transition portion having a contour corresponding to a contour of the bone fracture to be fused;
   a first staple leg extending from the first end portion to a first distal tip in the second direction, wherein the first staple leg has a first staple leg height extending from the bridge to the first distal tip;
   a second staple leg extending from the second end portion to a second distal tip in the second direction, wherein the second staple leg has a second staple leg height extending from the bridge to the second distal tip, and wherein the first staple leg height is greater than the second staple leg height; and
   a central portion disposed along the bridge between the first staple leg and the second staple leg, the central portion having a structure that supports boney ingrowth, wherein a thickness of the central portion is in a range between 0.5 mm and 4.0 mm.

8. An orthopedic staple for fusion of a foot or ankle bone fracture, the staple comprising:
   a bridge extending from a first end portion to a second end portion along a first direction, the bridge including a step down region between the first end portion and the second end portion, wherein the step down region extends in both the first direction and a second direction that is different from the first direction, the step down region including a transition portion having a contour corresponding to a contour of the bone fracture to be fused;
   a first staple leg extending from the first end portion to a first distal tip in the second direction, wherein the first staple leg has a first staple leg height extending from the bridge to the first distal tip;
   a second staple leg extending from the second end portion to a second distal tip in the second direction, wherein the second staple leg has a second staple leg height extending from the bridge to the second distal tip, and wherein the first staple leg height is greater than the second staple leg height; and
   a central portion disposed along the bridge between the first staple leg and the second staple leg, the central portion having a structure that supports boney ingrowth, wherein a height of the step down region is in a range is less than 4.0 mm.

9. An orthopedic staple comprising:
   a bridge extending from a first end portion to a second end portion, the first end portion having a first surface lying in a first plane, and the second end portion having a second surface lying in a second plane, the bridge further including a step down region between the first end portion and the second end portion that causes a disparity between a location of the first plane and a location of the second plane, wherein the step down region includes a transition surface between the first surface and the second surface having a contour;
   a first staple leg extending away from the first end portion to a first distal tip, wherein the first staple leg has a first staple leg height extending from the bridge to the first distal tip;
   a second staple leg extending away from the second end portion to a second distal tip, wherein the second staple leg has a second staple leg height extending from the bridge to the second distal tip, and wherein the first staple leg height is greater than the second staple leg height; and
   wherein the staple is sized to be inserted at least one of a talonavicular (TN) fusion, a calcaneus/cuboid (CC)

fusion, a tibia/talus (TT) fusion, a tarsal/metatarsal (TMT) fusion, a navicular cuneiform (NC) fusion, 1st, 2nd, 3rd, Lapidus (fusion of the metatarsal/cuneiform), a Lisfranc procedure or a calcaneus slide, and wherein the bridge is shaped corresponding to an anatomical structure of a bone surface surrounding the insertion site and the contour is shaped corresponding to a contour of the bone fracture to be fused, wherein the transition surface of the staple corresponds to the contour of the bone fracture to be fused according to anatomic data stored in an anatomic database.

10. The staple of claim 9, further comprising a central portion disposed along the bridge between the first staple leg and the second staple leg, the central portion having a structure that supports boney ingrowth.

11. The staple of claim 9, further comprising a central portion disposed along the bridge between the first staple leg and the second staple leg, the central portion comprising a core and a structure around the core that supports boney ingrowth.

12. The staple of claim 11, wherein the central portion comprises a porous structure.

13. The staple of claim 9, wherein the first staple leg and the second staple leg are formed of solid titanium.

* * * * *